United States Patent [19]

Kirchner

[11] Patent Number: 4,583,970
[45] Date of Patent: Apr. 22, 1986

[54] MILK SUCTION DEVICE

[75] Inventor: Hansjörg Kirchner, Markgröningen, Fed. Rep. of Germany

[73] Assignee: Kirchner & Wilhelm, Stuttgart, Fed. Rep. of Germany

[21] Appl. No.: 737,176

[22] Filed: May 23, 1985

[30] Foreign Application Priority Data

May 25, 1984 [DE] Fed. Rep. of Germany ....... 3419613

[51] Int. Cl.$^4$ .............................................. A61M 1/06
[52] U.S. Cl. ....................................... 604/74; 604/184
[58] Field of Search ................................. 604/74–76, 604/184, 316

[56] References Cited

U.S. PATENT DOCUMENTS 3,782,385 1/1974 Loyd ...................................... 604/74
4,287,819 9/1981 Emerit ............................. 604/316 X
4,311,141 1/1982 Diamond ............................... 604/74
4,457,755 7/1984 Wilson ................................. 604/184

Primary Examiner—Dalton L. Truluck
Attorney, Agent, or Firm—Toren, McGeady, Stanger, Goldberg & Kiel

[57] ABSTRACT

A milk suction device consisting of a funnel and a piston pump connected thereto which can be operated easily as a hand-operated pump or as a motor driven pump. A hollow piston rod is constructed as an outwardly guided aeration duct and has a return valve as its opening located in the suction space of a cylinder of the pump, which return valve is closed during the suction stroke of the piston pump and is constructed as an aeration valve. A ventilation valve is arranged in a front face of the pump cylinder opposite the piston rod and in order to connect a motor driven pump, it is only necessary to slide its tube onto the free end of the piston rod.

6 Claims, 1 Drawing Figure

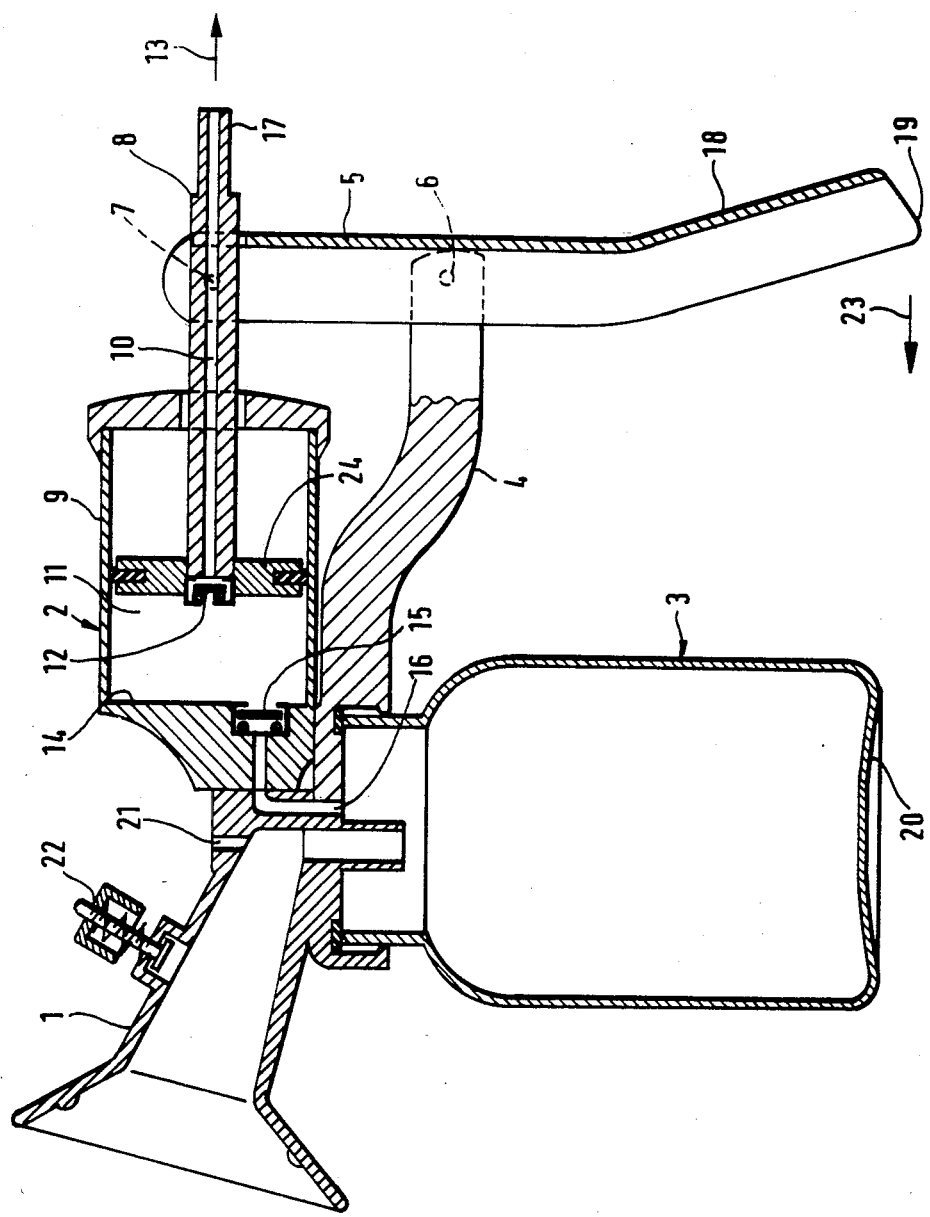

MILK SUCTION DEVICE

The present invention is directed to a milk suction device and particularly to a device comprising a funnel which may be placed on the human breast. The type of device to which the present invention relates comprises a pump which is then connected to the funnel and which generates a low pressure suction in the funnel.

In the prior art, in addition to relatively simple rubber ball pumps, manually actuated diaphragm and piston pumps are also used. Suction devices with manually actuable pumps which can be operated, in addition, with a motor driven pump are also known. However, for this purpose, these devices require either adapters or exchange of entire parts. As a result of the somewhat complicated handling, therefore, the capability for motor drive is rarely made use of in actual practice.

SUMMARY OF THE INVENTION

The invention proceeds from a milk suction device consisting of a funnel, a piston pump with a piston rod and an aeration and ventilation valve, the piston pump being connected at the funnel. The invention is directed toward providing a device which, on the one hand, generates a low pressure, which is as constant as possible, and, on the other hand, can be connected without great expenditure at a desired motor driven pump.

This object is met in that the hollow piston rod is constructed, according to the invention, as an outwardly guided aeration duct and has at its opening into the suction space a return or check valve constructed as an aeration valve which is closed during the suction stroke. By means of the arrangement of two valves, it is possible, in contrast to other devices of this type, to continuously maintain low pressure in order to prevent fluctuation of the low pressure which is unpleasant for the user.

A motor operated pump can now be attached in a particularly simple manner. It may merely be connected with the outwardly projecting hollow piston rod, without requiring converting of the device. The ventilation valve is preferably arranged in the front face of the pump cylinder remote of the piston rod so that the entire cylinder space is available for the piston stroke.

According to another characteristic feature of the invention, the piston rod is connected in an articulated manner with one end of a double-armed, swivel lever whose other end is constructed as a handle. By means of this, in contrast to other pumps, the funnel is pressed on the breast during the suction process and is not pulled away from it, so that a tight support is ensured. The outwardly guided end of the piston rod is preferably constructed as an attaching sleeve for the suction tube of a motor driven pump and projects beyond the articulating point of the lever. In this way, the tube of a motor driven pump can be connected easily and particularly without the actuating lever creating a disturbing effect.

According to another characteristic feature of the invention, the lever part which is constructed as a handle is constructed at its free end as a support and at a length such that it lies approximately in a plane level with the bottom or base of a milk collecting container or vessel attached at the suction device. By means of this, the suction device can be used without overturning. An excess pressure valve or relief valve, particularly one that is adjustable, is preferably arranged at the funnel. This prevents the low pressure produced by the arrangement of the ventilation and aeration valve from becoming too strong and injuring the user.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there is illustrated and described a preferred embodiment of the invention.

DESCRIPTION OF THE DRAWING

In the drawing:

FIG. 1 is a schematic cross-sectional view showing a preferred embodiment of the invention.

DETAILED DESCRIPTION OF THE PREFERRED EMBODIMENT

Referring now to FIG. 1, the invention is shown as comprising a funnel 1 attached to a milk collecting container 3 having a piston pump 2 attached thereto.

The funnel 1, which may be placed on a human breast, is joined with the piston pump 2 and the entire assembly is screwed onto the milk collecting container 3.

Located beneath the piston pump 2 is a rearwardly projecting carrying arm 4 at which a double-armed lever 5 is swivelably supported at 6. The latter is connected at its upper end in an articulated manner at 7 with the piston rod 8 which projects rearwardly out of the cylinder 9 of the pump 2. The piston rod 8 is constructed so as to be hollow and has an aeration duct 10 which connects a suction space 11 of the cylinder 9 with the outer surrounding air. A return valve 12 for aeration, which closes in the direction of arrow 13 during the suction stroke, is arranged at the end of the piston rod 8 opening into the suction space 11. A ventilation valve 15, which is likewise constructed as a return valve and is connected with the milk collecting container 3, and, accordingly, with the funnel 1, via duct 16, is provided in the front face 14 of the cylinder 9, which front face 14 is remote from the piston 8.

The rear free end 17 of the piston rod 8 is reduced and tapers and is constructed as an attaching sleeve for the tube of a motor driven pump (not shown). The lower part 18 of the lever 5 serves as a handle and its lower end 19 is shaped as a support. When the lever 5 in the example shown in the drawing is located in one of its end positions, the support 19 lies approximately in a plane level with the bottom 20 of the milk collecting container 3, so that the lever 5 serves as a supporting device for the pump 2 which projects considerably beyond the area of the base of the milk collecting container 3.

A ventilation opening 21 is provided at the funnel 1, which ventilation opening 21 can be covered by the hand and serves to adjust the correct low pressure. In order to safely exclude injury to the breast as a result of excessive low pressure, a return valve 22 is additionally provided at the funnel whose spring plate can be adjusted so that it is possible to set and adjust the maximum pressure. Additional air can then enter from the outside at this valve when the low pressure or suction is too strong.

In order to draw milk, the funnel 1 is placed on the breast, the opening 21 is sealed by means of a finger and the handle 18 of the lever 5 is moved in a reciprocating motion. When the handle 18 of the lever 5 is pressed in the direction of arrow 23, that is, against the breast, the piston rod 8 moves in the direction of arrow 13 and carries along the piston 24. In so doing, the aeration valve 12 closes and the ventilation valve 15 opens, so that a low pressure or suction occurs in the funnel. In so doing, the milk is drawn in and runs into the container 13. When the handle 18 is moved in the opposite direction, the ventilation valve 15 closes and the aeration valve 12 opens, so that the piston 24 is moved into its forward position. The funnel 1 and the milk collecting container 3 are outwardly sealed by means of the breast and the valve 22, so that the low pressure is maintained to the extent that it is not changed by releasing the opening 21.

To the extent that a motor driven pump is used, a tube of this pump (not shown) must merely be placed onto the free end 17 of the piston rod 8. During the suction process, both valves 12 and 15 open so that no other measures, e.g., the arrangement of an adapter or the like, are required. In order to put away the device, the handle 18 is brought into one of the end positions and then serves as a support in order to receive the weight of the projecting piston pump 2.

While a specific embodiment of the invention has been shown and described in detail to illustrate the application of the inventive principles, it will be understood that the invention may be embodied otherwise without departing from such principles.

What is claimed is:

1. A milk suction device comprising: a funnel adapted to receive milk therethrough; a container connected to said funnel for receiving milk therefrom; a piston pump attached to said container for creating a suction therein to draw milk through said funnel; said piston pump comprising a cylinder, a piston movable within said cylinder and a hollow piston rod defining therethrough an aeration duct having one end in flow communication with said cylinder and an opposite end vented to the exterior of said cylinder, said piston being movable within said cylinder through a suction stroke and a return stroke; and a return valve connected at said one end of said aeration duct, said return valve being constructed as an aeration valve and being closed during said suction stroke of said piston.

2. A device according to claim 1, wherein said cylinder comprises a front face which is located on a side of said piston remote from said piston rod, said device further comprising a ventilation valve arranged in said front face of said cylinder in flow communication between the interior of said cylinder and said container.

3. A device according to claim 1, further comprising a double-armed swiveling support lever having an end constructed as a handle, said piston rod being connected in an articulated manner with the other end of said lever.

4. A device according to claim 1, wherein said piston rod extends outwardly from said cylinder and is constructed as an attachment sleeve for the suction tube of a motor driven pump, whereby said suction tube may be connected in flow communication with said aeration duct.

5. A device according to claim 3, wherein said end of said lever constructed as a handle is configured with a free end adapted to operate as a support and having a length such that it lies in a plane approximately level with the bottom of said container at least in one position of said handle.

6. A device according to claim 1, further comprising an excess pressure valve adapted for adjustable operation arranged in said funnel.

* * * * *